US009854721B2

(12) United States Patent
Smeets (10) Patent No.: US 9,854,721 B2
(45) Date of Patent: Jan. 2, 2018

(54) SHARE TIP AND TOOL COMBINATION HAVING A SHARE TIP (71) Applicant: BETEK GMBH & CO. KG, Aichhalden (DE)

(72) Inventor: Florian Smeets, Baiersbronn (DE)

(73) Assignee: Betek GmbH & Co. KG, Aichhalden (DE)

( * ) Notice: Subject to any disclaimer, the term of this patent is extended or adjusted under 35 U.S.C. 154(b) by 0 days.

(21) Appl. No.: 14/774,237

(22) PCT Filed: Feb. 5, 2014

(86) PCT No.: PCT/EP2014/052237
§ 371 (c)(1),
(2) Date: Sep. 10, 2015

(87) PCT Pub. No.: WO2014/139733
PCT Pub. Date: Sep. 18, 2014

(65) Prior Publication Data
US 2016/0014950 A1  Jan. 21, 2016

(30) Foreign Application Priority Data

Mar. 11, 2013  (DE) .......................... 10 2013 102 420

(51) Int. Cl.
*A01B 15/06* (2006.01)
*A01B 15/02* (2006.01)
*A01B 23/02* (2006.01)
*A61C 8/00* (2006.01)
*A61C 13/00* (2006.01)
(Continued)

(52) U.S. Cl.
CPC .............. *A01B 15/06* (2013.01); *A01B 15/02* (2013.01); *A01B 15/10* (2013.01); *A01B 23/02* (2013.01); *A01B 39/22* (2013.01); *A61C 8/006* (2013.01); *A61C 8/0068* (2013.01); *A61C 13/0022* (2013.01)

(58) Field of Classification Search
CPC ....... A01B 35/225; A01B 35/26; A01B 39/22; A01B 23/02; A61C 8/006; A61C 8/0068; A61C 13/0022
See application file for complete search history.

(56) References Cited

U.S. PATENT DOCUMENTS 1,132,335 A * 3/1915 Graves ................. A01B 35/225
172/751
2,302,785 A * 11/1942 Mansur .................. A01B 35/26
172/730
(Continued)

FOREIGN PATENT DOCUMENTS

DE  196 39 862 A1  4/1998
DE  100 18 279 A1  10/2001
(Continued)

*Primary Examiner* — Jamie L McGowan
(74) *Attorney, Agent, or Firm* — Pauley Erickson & Kottis (57) ABSTRACT A tool combination, including a share tip and an adjoining guide element, wherein the share tip and the guide element have threaded receptacles for fastening to a tine. An easy and secure fastening of both the share tip and the guide element is achieved according to this invention if the guide element has a threaded receptacle which is covered in the tool advancement direction by a cover portion of the share tip.

21 Claims, 5 Drawing Sheets (51) Int. Cl.
*A01B 15/10* (2006.01)
*A01B 39/22* (2006.01)

(56) References Cited

U.S. PATENT DOCUMENTS

| | | | | |
|---|---|---|---|---|
| 2,877,061 A * | 3/1959 | Blackwood | ............ | A01B 39/22 172/732 |
| 3,061,021 A * | 10/1962 | Shader | ................ | A01B 35/225 172/750 |
| 3,536,147 A * | 10/1970 | Olson | .................... | A01B 13/08 172/719 |
| 4,779,686 A * | 10/1988 | Ryan | .................... | A01B 35/225 172/730 |
| 4,867,248 A * | 9/1989 | Robertson | ............ | A01B 15/025 172/721 |
| 5,007,484 A * | 4/1991 | Johanson | ............. | A01B 35/225 172/1 |
| 5,465,796 A * | 11/1995 | Buescher | ............. | A01B 35/225 172/730 |
| 5,558,165 A * | 9/1996 | Bucher | ................ | A01B 35/225 172/721 |
| 5,711,378 A * | 1/1998 | Yeager | ................ | A01B 35/225 172/730 |
| 5,941,318 A * | 8/1999 | Bergen | ................. | A01B 35/225 172/730 |
| 6,289,996 B1 * | 9/2001 | Parish | ................... | A01B 35/225 172/730 |
| 6,315,058 B1 * | 11/2001 | Birkenbach | .......... | A01B 35/225 172/753 |
| 6,585,058 B2 * | 7/2003 | Zaun | ..................... | A01B 35/225 172/750 |
| 6,668,940 B1 * | 12/2003 | Ryan | .................... | A01B 15/025 172/751 |
| 6,684,963 B1 * | 2/2004 | Poutre | ................. | A01B 35/225 172/750 |
| 7,070,007 B2 * | 7/2006 | Poutre | ................. | A01B 35/225 172/750 |
| 7,255,179 B2 * | 8/2007 | Pollard | ................ | A01B 35/225 172/683 |
| 7,770,657 B2 * | 8/2010 | Poutre | .................... | A01B 35/26 172/724 |

FOREIGN PATENT DOCUMENTS

DE 10 2011 102 053 A1 11/2012
FR 2 254 261 A1 7/1975

* cited by examiner

SHARE TIP AND TOOL COMBINATION HAVING A SHARE TIP

BACKGROUND OF THE INVENTION

Field of the Invention

This invention relates to a share tip for an agricultural soil cultivating machine, having a base part that has a blade on a blade holder, and the base part has a threaded opening for fastening to a support, in particular a tine of the agricultural soil cultivating machine.

This invention also relates to a tool combination having a share tip and a guide element attached thereto, and the share tip and the guide element have threaded openings for fastening to a tine.

Discussion of Related Art

German Patent Reference DE 10 2011 102 053 A1 discloses a tool combination having a share tip and a guide plate, which can be fastened together to a tine of a soil cultivating machine. At a blade end, the share tip has a blade holder equipped with a blade element composed of hard metal. To the sides of the blade element, secondary blades are soldered to the blade holder at an angle. The blade holder has a threaded opening, which can be oriented so that it is flush with a threaded opening of the guide plate. The guide plate is placed onto the share tip and covers the areas of the surface adjacent to the blade and the secondary blades. In order to fasten the combination of the guide plate and the share tip, a fastening screw is inserted from the front through the flush threaded openings of the guide plate and the share tip and is screwed into a threaded opening of the tine. In harsh operating conditions and difficult ground conditions, the guide plate may be bent relative to the share tip and shorn off. This then causes a significant impairment to the functionality of the tool combination.

SUMMARY OF THE INVENTION

One object of this invention is to provide a share tip of the type mentioned above and a tool combination having a share tip, which makes it possible to securely fasten the guide element and the share tip to a tine or similar support of an agricultural soil cultivating machine and in which at least one securing element is protected from wear.

The above object and others according to this invention relating to the share tip is achieved if the base part has a recess, which is covered in the tool advancement direction by a covering section. The guide element can thus be accommodated with its free end protected behind the covering section. The guide element and securing element or screw in this region are thus protected from being struck by the soil material that is dug up by the share tip. In particular, the guide element then can no longer be bent or twisted at its free end relative to the share tip, thus assuring long-term functionality.

According to one embodiment of this invention, it is possible for the recess to be open toward the back of the base part and for it to constitute or form an insertion socket from the side. The guide element is thus accommodated so that it is protected laterally as well and can be guided out of the recess region through the opening side.

According to another embodiment of this invention, a share tip can be embodied so that the recess has at least one locking piece to provide a form-fitting locking of a guide element perpendicular to the tool advancement direction. With the locking piece, it is possible to secure the guide element and share tip to each other perpendicular to the advancement direction, thus achieving a reduction in the required number of fasteners, in particular fastening screws.

In another embodiment of this invention, in the region of the recess, two locking pieces are used, which are spaced apart from each other perpendicular to the tool advancement direction. The guide element can then be enclosed between the two locking pieces.

A stable tool design is achieved if in the region of or near the covering section, two locking pieces are formed onto the back side of the base part and the locking pieces constitute support surfaces. The guide element can be exactly aligned with the support surfaces. Because the locking pieces protrude from the back of the base part, the recess can be easily produced. In particular, the share tip can then be produced as a forged part with a low tool cost.

A further stabilization of the locking pieces can be achieved if the recess has a connecting section, which connects the locking pieces to each other in integral fashion. This makes it possible to reliably carry away transverse forces.

To simplify assembly, it is possible for an insertion socket of the recess to be laterally bordered by insertion bevels that are spaced apart from each other. Then the share tip can be attached to the guide element in a simple way.

A share tip according to this invention can be embodied so that in front of the threaded opening in the tool advancement direction, a projection is provided, which protrudes up from a deflection surface of the share tip. The projection serves as a deflector for the soil material and guides it away from a screw head that is mounted in the threaded opening. The screw head is thus positioned in a way that protects it from wear.

One object of this invention is also attained with a tool combination in which the guide element has a threaded opening, which is covered by a covering section of the share tip. In this case, the covering section is positioned in front of the guide element in the tool advancement direction so that it can be accommodated there in a protected way. As mentioned above, the guide element is thus protected from being struck by the soil material flowing past the guide element.

In one possible variant of this invention, one or more locking pieces lock the share tip and the guide element to each other in a form-fitting fashion perpendicular to the tool advancement direction. Preferably, the share tip in this case is equipped with only one threaded opening. It is thus possible to reduce the number of required fastening elements in connection with the form-fitting locking action. The share tip can be simply attached to a mounted guide element if, in the region of its end oriented toward the share tip, the guide element has an insertion projection that is inserted laterally into the recess.

The assembly is particularly simple if the insertion projection has two guide bevels that are arranged in a V shape relative to each other.

A further service life optimization for the guide element can be easily achieved if in the connecting region to the share tip, a hard material element is mounted on the guide element. The hard material element can, for example, be an armored layer, in particular a deposit weld, or it is conceivable to mount hard material elements made of hard metal or the like to the guide element.

BRIEF DESCRIPTION OF THE DRAWINGS

This invention is explained in greater detail below in view of an exemplary embodiment shown in the drawings, wherein.

DETAILED DESCRIPTION OF THE INVENTION

Figure 1:
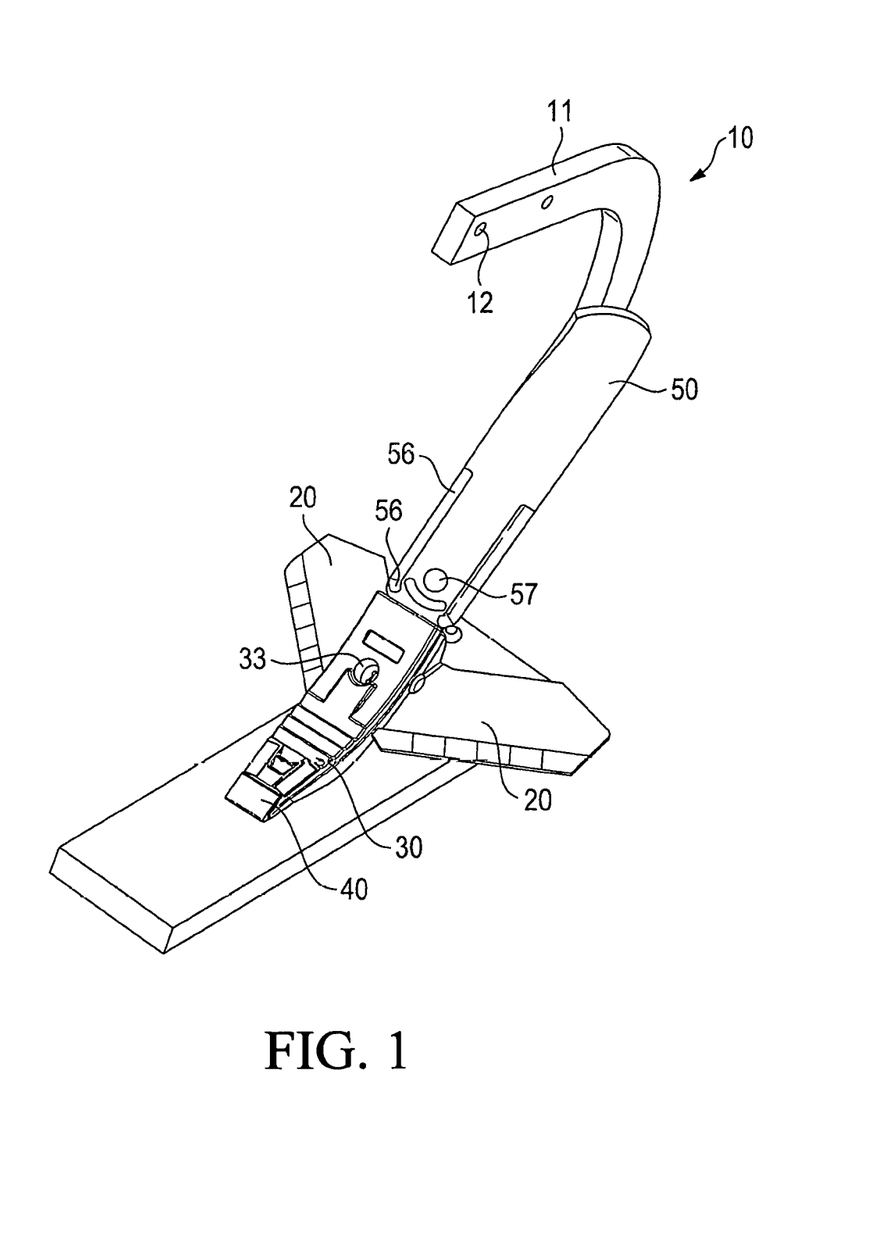
FIG. 1 is a perspective front view of a cultivator blade with a share tip and a guide element.

FIG. 1 shows a cultivator blade for installation on a tool holder, in particular a tine 10 or tine holder or plow beam or the like of an agricultural soil cultivating machine. The tine 10 has a fastening part 11, which has threaded openings 12 passing through it. With these threaded openings 12, the tine 10 can be mounted on a device support. As FIG. 2 also shows, on the side oriented away from the fastening part 11, the tine 10 has a support piece 13. A share tip 30, a guide element 50, and two plow wings 20 can be mounted onto this support piece 13.

The plow wings 20 have a transverse support 21 to which blade elements 22 made of a hard material are fastened. Preferably, the blade elements 22 are made of a hard metal that is integrally joined to the transverse support 21, in particular soldered to it. The transverse support 21 has an angle piece 23 bent up from it, which is equipped with threaded openings. The plow wings 20 can be fastened to the tine 10 by fastening screws 14 that are inserted through the threaded openings of the angle piece 23 and the threaded openings of the support piece 13. The guide element 50 with the fastening part 11 is mounted above the plow wings 20.

Figure 2:
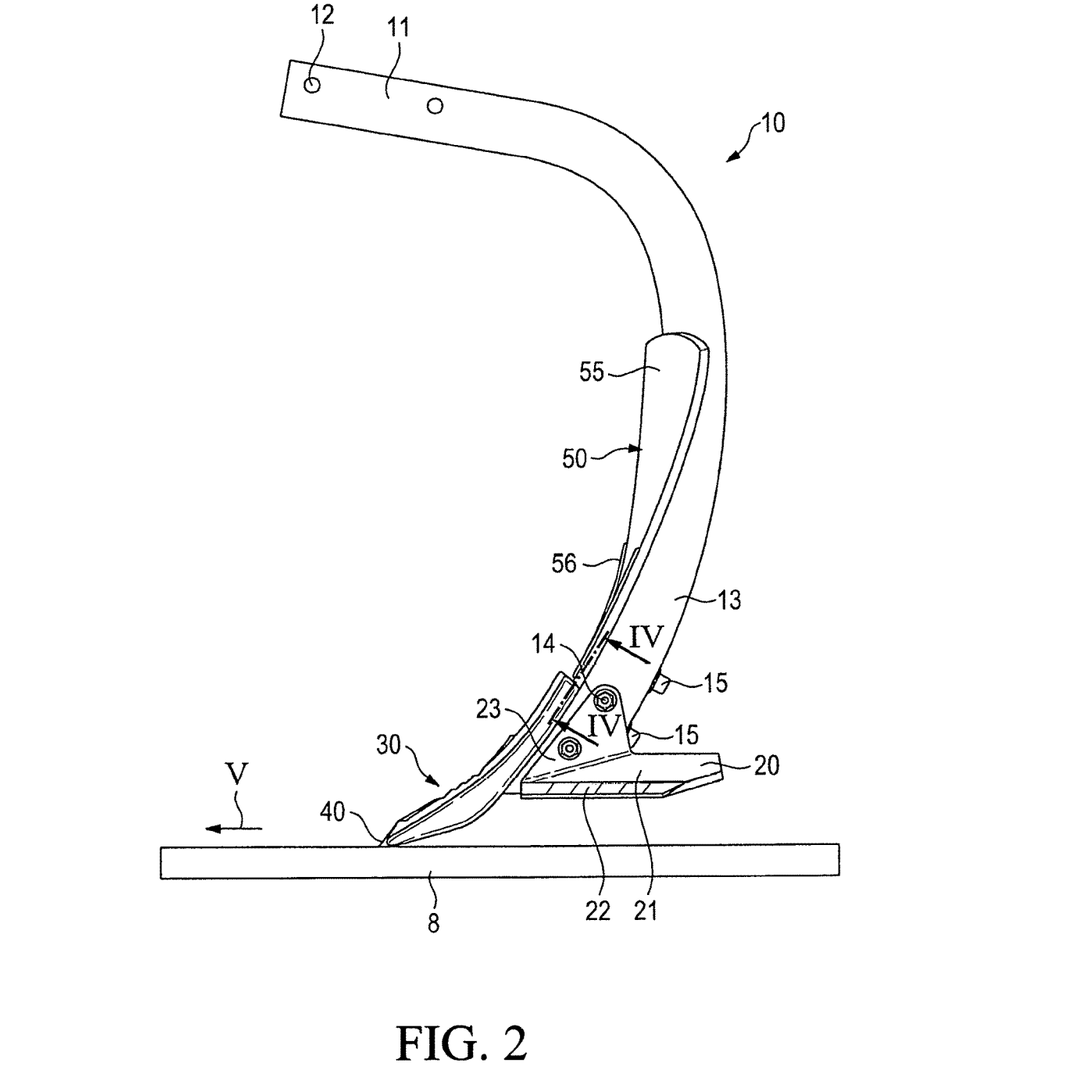
FIG. 2 is a side view of the depiction shown in FIG. 1.

As shown in FIGS. 1 and 2, the guide element 50 is composed of or comprises a sheet-like forged steel component. It is curved so that it forms a helical deflection surface 55. Sometimes, rectilinear deflection surfaces are also used. Hard material elements 56 in the form of a deposit weld are attached to this deflection surface. The guide element 50 also has a threaded opening 57 that is clearly visible in FIG. 1. A fastening screw can be inserted through the threaded opening 57. This fastening screw is guided through a threaded opening of the support piece 13 and secured by a nut. FIG. 1 shows that an arc-shaped hard material element 56, particularly in the form of a deposit weld or hard metal elements, is situated or positioned in front of the threaded opening 57 in the tool advancement direction V (tool advancement direction V, indicated in FIG. 2). This hard material element 56 serves as a deflector for soil flowing past or beyond. The screw head of the fastening screw 15, which is secured in sunken fashion in the threaded opening 57, is thus protected from the abrasive wear of the soil.

Figure 3:
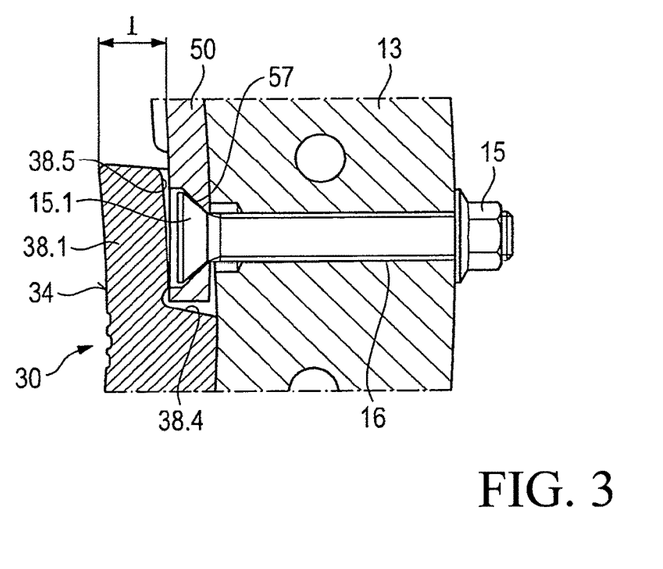
FIG. 3 is an enlarged view of a detail labeled III-III in FIG. 4.

As shown in FIGS. 2 and 3, the guide element 15 is also fastened to the tine 10 by a second fastening element, in particular a fastening screw 15. The guide element 50 has another threaded opening 16 for this purpose. This threaded opening 16 is situated or positioned flush with a threaded opening 57 of the support piece 13 of the tine 10. A fastening screw 15 can be inserted through the flush threaded openings 57 and 16 and secured at the back with a nut. The two fastening elements 15 thus securely attach the guide element 50 at two fixing points. As shown in FIG. 3, the fastening elements 15 are embodied in the form of fastening screws equipped with a screw head 15.1. The geometric embodiment of the screw head 15.1 and the threaded opening 57 is such that the screw head 15.1 is either essentially flush with the surface of the front of the guide element 50 or is accommodated in a recessed fashion. This is clearly shown in FIG. 3.

Figure 4:
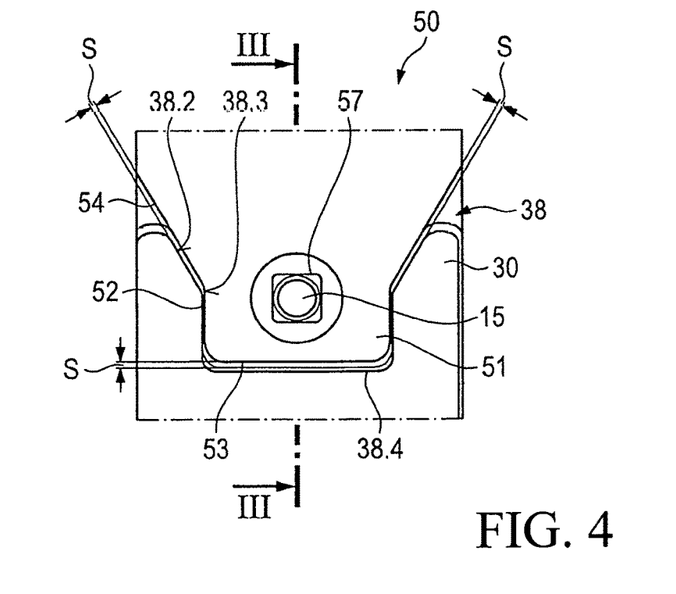
FIG. 4 is an enlarged view of a detail labeled IV-IV in FIG. 2.

FIG. 4 also shows that the threaded opening 57 is provided in an insertion projection 51 of the guide element 50. The insertion projection 51 has two guide bevels 54 that are arranged in a V shape relative to each other and they transition into side pieces 52. The side pieces 52 are situated in the region of an end 53 of the insertion projection 51.

Figure 5:
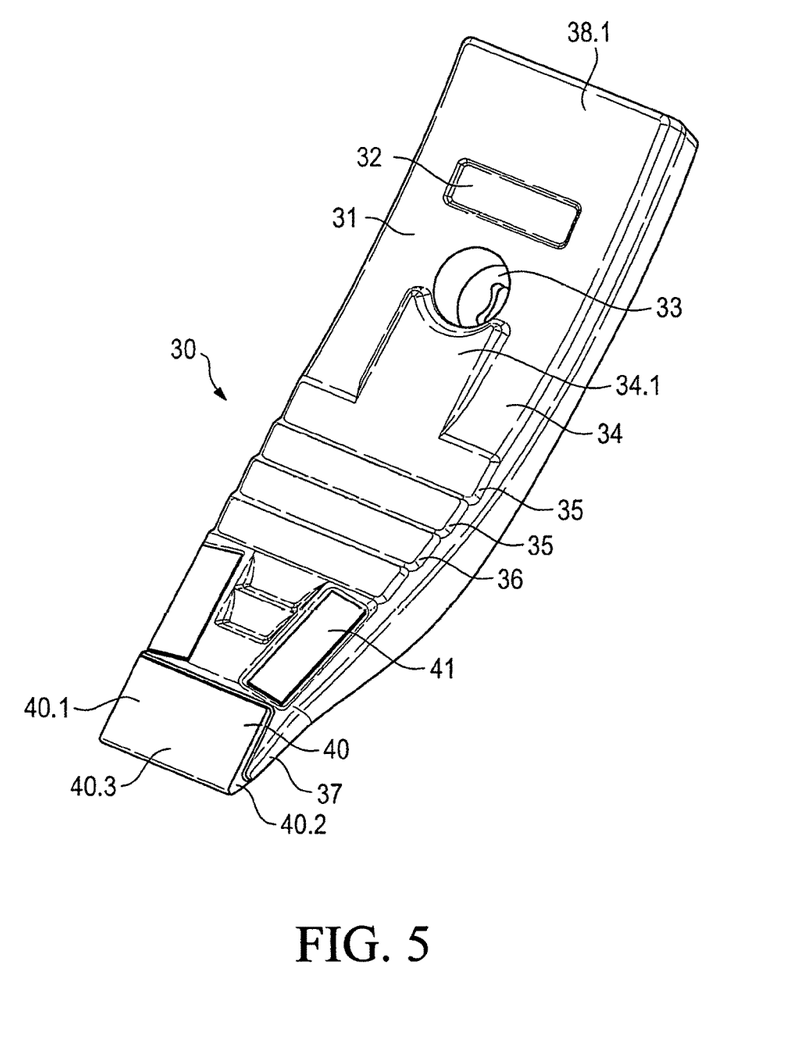
FIG. 5 is a perspective detailed front view of the share tip of the cultivator blade according to FIG. 1.

In order to complete the cultivator blade, a share tip 30 is mounted to the tine 10. The design of the share tip 30 is shown in greater detail in FIGS. 5 and 6. As these drawings show, the share tip 30 has a base part 31 through which a threaded opening 33 passes. An identification field 32 is provided above the threaded opening 33. Below the threaded opening 33, there is a projection 34.1, which in the form of a deflector, protrudes up from the front deflection surface 34 of the base part 31. In this way, the projection 34.1 constitutes or forms an apron that protects a screw head situated in the threaded opening 33 from the abrasive action of the soil flowing past. In front of the projection 34.1 in the advancement direction, the base part 31 has steps 35 that protrude up from the deflection surface 34. In the present exemplary embodiment, the steps 35 are rib-shaped and oriented perpendicular to the tool advancement direction. There are hollows 36 between the individual steps 35. During use of the tool, soil can be compressed into the region of the hollows 36 and accumulate there. This forms a type of natural wear protection on the deflection surface 34. In front of the steps 35 in the tool advancement direction, the base part 31 has a blade holder 37. Blade elements 40 in the form of hard metal elements are fastened to the blade holder 37. The blade elements 40 have a sheet-like fastening section 40.1 and formed onto the latter, a shoulder 40.2 protruding away from the tool advancement direction V. A blade 40.3 is produced in the region of or near the shoulder 40.2. The blade elements 40 are fastened to the blade holder 37 so that the free terminal edge of the blade holder 37 is at least partially enclosed by the shoulders 40.2 of the blade elements 40, as is clearly shown FIG. 2 and also FIG. 6. This protects from wear the free end of the blade holder 37. Behind the blade elements 40 in the advancement direction, hard material elements 21 are mounted onto the edge regions of the base part 31 that are subjected to particularly intense wear. In the present case, hard material elements 41 embodied in the form of hard metal plates are soldered to the base part 31. It is also possible, however, to use an armored weld or the like.

Figure 6:
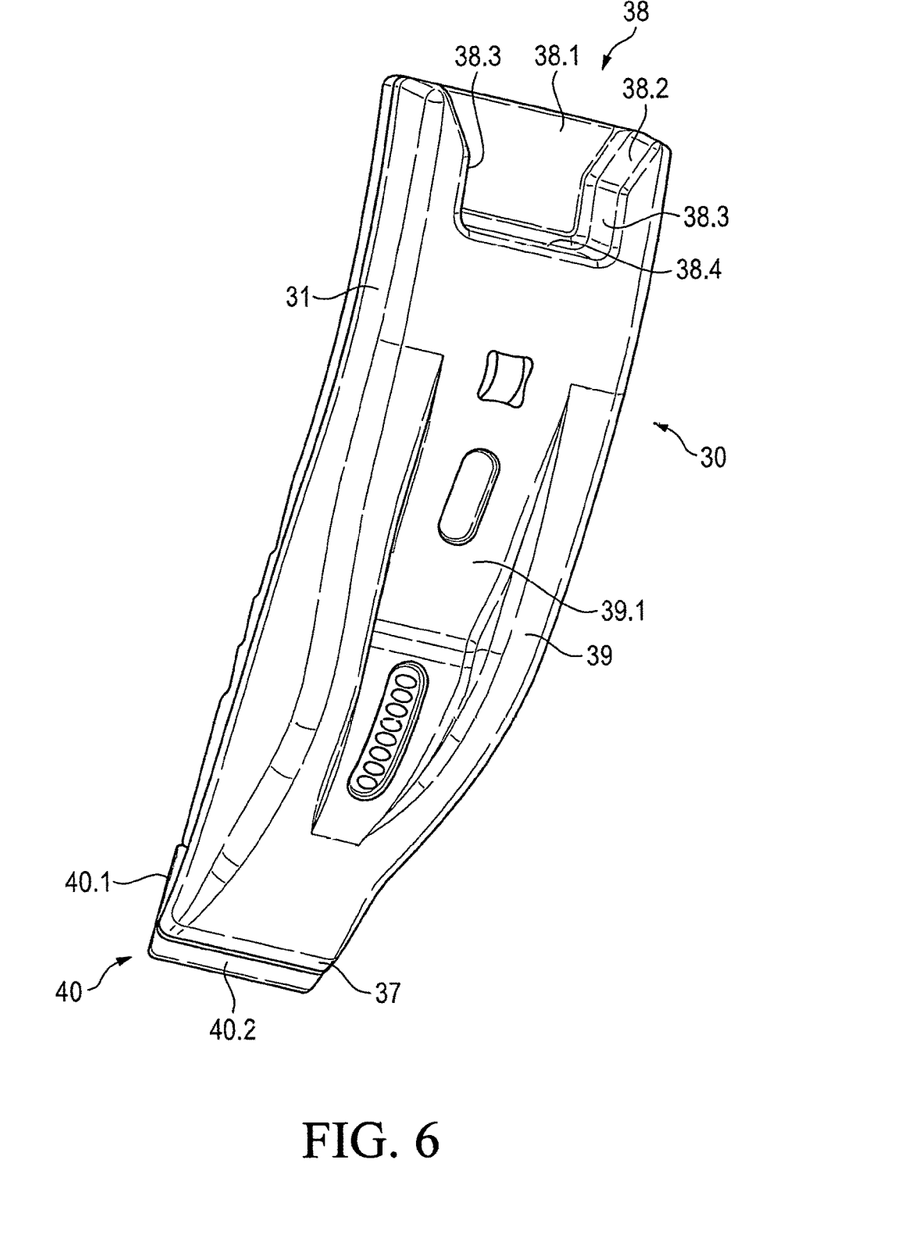
FIG. 6 is a perspective rear view of the share tip according to FIG. 5.

FIG. 6 shows a rear view of the share tip 30. As is clear from this depiction, projections 39 are formed onto the base part 31 in the region above the blade holder 37. The projections 39 are embodied in the form of ribs and are situated in the region of the longitudinal edges of the base part 31. The projections 39 are spaced apart from each other so that a slot 39.1 is formed between the projections 39. At the end oriented away from the blade holder 37, the share tip 30 has a recess 38. The recess 38 is formed in a pocket shape into the back of the share tip 38. It has a covering section 38.1. The covering section 38.1 is adjoined at the sides by insertion bevels 38.2 in the form of wall elements. The wall elements in this case are arranged in a V shape relative to each other. Locking pieces 38.3 are situated in the region below the insertion bevels 38.2. The locking pieces 38.3 are spaced apart from each other and are likewise composed of or comprise wall elements that rise up from the covering section 38.1. The two locking pieces 38.3 are integrally joined to each other by a bottom 38.4 of the recess 38.

In order to assemble the share tip 30, the recess 38 is slid onto the insertion projection 51 of the guide element 50. As shown in FIG. 4, in this joining motion, the insertion projection 51 of the guide element 50 can be threaded into the insertion bevels 38.2, thus enabling a precise assembly. After the insertion projection 51 has passed the insertion bevels 38.2, the end 53 of the insertion projection 51 slides between the two locking pieces 38.3. In this case, the dimensional association is selected so that the locking pieces 38.3 are laterally associated with the side pieces 52. As a result, the share tip, taking into account a design-required minimal play, is fixed against the locking pieces 38.3 in a form-fitting fashion perpendicular to the tool advancement direction. In order to provide a definite seat in this case, the bottom 38.4 and the end 53 of the insertion projection 51 are spaced apart from each other (see the play or space S in FIG. 4). The insertion bevels 38.2 are also situated so that they are spaced slightly apart from the guide bevels 54 (see the play or space S in FIG. 4).

After the recess 38 of the share tip 30 has been affixed to the insertion projection 51 of the guide element 50, the threaded opening 33 of the share tip 30 is situated flush with a threaded opening of the tine 10. Then a fastening screw can be inserted through the flush threaded openings and the share tip 30 can be affixed to the tine 10 with only one fastening screw. The rotationally secured association of the share tip 30 with the tine 10 is thus ensured by the form-fitting locking action between the insertion projection 51 and the recess 38.

In the assembled state, the share tip 30 protrudes up from the surface of the guide element 50 in the region of or near the recess 38 with its deflection surface 34 that ends there. As shown in FIG. 3, this produces a shoulder with a protrusion T. This protrusion T once again serves as a deflector, which deflects soil away from the screw head, which is secured in the threaded opening 57 (see FIG. 1). In order to be able to reliably fulfil this function, the spacing dimension T should be at least 8 mm. An optimal wear protection is achieved with a protrusion >12 mm.

The invention claimed is:

1. A share tip (30) for an agricultural soil cultivating machine, comprising:
   a base part (31) including a blade holder (37) at a first end and which has a blade (40.3), the base part (31) including a screw opening (33) for fastening to a support tine (10) of the agricultural soil cultivating machine; and
   the base part (31) having a recess (38) at a second end opposite the first end, the recess covered in a tool advancement direction (V) by a covering section (38.1) and the recess disposed between the covering section and the support tine;
   wherein a back surface of the base part is fastenable on the support tine, and the recess (38) is formed in the back surface open toward the back of the base part (31), and forms an insertion socket at the second end between the covering section and the support tine.

2. The share tip according to claim 1, wherein the recess (38) has at least one locking piece (38.3) to provide a form-fitting locking of a guide element (50) perpendicular to the tool advancement direction.

3. The share tip according to claim 2, wherein the recess has two locking pieces (38.3) spaced apart from each other and perpendicular to the tool advancement direction.

4. The share tip according to claim 2, wherein near the covering section (38.1), two locking pieces (38.3) are formed onto the back side of the base part (31), and the locking pieces (38.3) form support surfaces.

5. The share tip according to claim 4, wherein the recess (38) has a connecting section (38.4) which integrally connects the locking pieces (38.3) to each other.

6. The share tip according to claim 5, wherein an insertion socket of the recess is laterally bordered by insertion bevels (38.2) spaced apart from each other.

7. The share tip according to claim 6, wherein in front of the screw opening (33) in the tool advancement direction (V) is a projection (34.1) which protrudes up from a deflection surface (34).

8. The share tip according to claim 1, wherein the recess (38) has at least one locking piece (38.3) to provide a form-fitting locking of a guide element (50) perpendicular to the tool advancement direction.

9. The share tip according to claim 1, wherein an insertion socket of the recess is laterally bordered by insertion bevels (38.2) spaced apart from each other.

10. The share tip according to claim 1, wherein in front of the screw opening (33) of the share tip in the tool advancement direction (V) is a projection (34.1) which protrudes up from a deflection surface (34).

11. The share tip according to claim 1, wherein the back surface of the base part (31) comprises a slot (39.1) disposed between the recess and the blade holder, and adapted to receive the support tine.

12. A tool combination, comprising:
   a share tip (30) and a guide element (50), the share tip (30) and the guide element (50) including screw openings (33, 57) for fastening to a tine (10)
   the guide element (50) including one of the screw openings (57) covered in a tool advancement direction (V) by a covering section (38.1) of the share tip (30), wherein the covering section does not include any opening;
   wherein near an end oriented toward the share tip (30), the guide element (50) has an insertion projection (51) laterally inserted into a recess (38) formed in the share tip and between the covering section and the tine.

13. The tool combination according to claim 12, wherein one or more locking pieces (38.3) lock the share tip (30) and the guide element (50) to each other in a form-fitting fashion perpendicular to the tool advancement direction (V).

14. The tool combination according to claim 13, wherein the covering section (38.1) is at an end of the share tip (30) opposite a blade holder (37) and the share tip (30) has a screw opening (33) through the share tip and positioned between the covering section (38.1) and the blade holder (37).

15. The tool combination according to claim 12, wherein the insertion projection (51) has two guide bevels (54) arranged in a V shape relative to each other.

16. The tool combination according to claim 15, wherein in the connecting region to the share tip (30), the guide element (50) has a hard material element (56), in particular an armored layer or the like.

17. A tool combination, comprising:
   a share tip (30) and a guide element (50), the share tip (30) and the guide element (50) including screw openings (33, 57) for fastening to a tine (10)
   the guide element (50) including one of the screw openings (57) covered in a tool advancement direction (V) by a covering section (38.1) of the share tip (30), wherein the covering section does not include any opening and covers a recess (38);

wherein near an end oriented toward the share tip (30), the guide element (50) has an insertion projection (51) inserted into the recess (38) laterally.

18. The tool combination according to claim 12, wherein in the connecting region to the share tip (30), the guide element (50) has a hard material element (56), in particular an armored layer or the like.

19. A tool combination for a tine of an agricultural soil cultivating machine, the tool combination comprising:

a share tip (30) including a blade holder (37) at a first end and a recess (38) at a second end opposite the first end, the recess covered in a tool advancement direction (V) by a covering section, the share tip (30) further including a first screw opening (33) disposed between the covering section and the blade holder, for fastening the share tip to the tine;

a guide element (50) including an insertion projection (51) insertable into the recess (38) and including a deflection surface extending from the insertion projection and beyond the recess (38), the guide element having a second screw opening (57) for fastening the guide element to the tine (10), wherein the second screw opening (57) is covered in the tool advancement direction (V) by the covering section (38.1) of the share tip (30) when the insertion projection is inserted in the recess (38).

20. The share tip according to claim 19, wherein the covering section does not include any screw opening.

21. The share tip according to claim 19, wherein the back surface of the base part (31) comprises a slot (39.1) disposed between the recess and the blade holder, and adapted to receive the support tine.

* * * * *